United States Patent
Labrie et al.

(10) Patent No.: US 11,690,852 B2
(45) Date of Patent: Jul. 4, 2023

(54) REDUCTION OF THE INCIDENCE OR RECURRENCE OF BREAST CANCER IN POSTMENOPAUSAL WOMEN TREATED WITH INTRAVAGINAL SEX STEROID PRECURSOR

(71) Applicant: Endorecherche, Inc., Québec (CA)

(72) Inventors: Fernand Labrie, Québec (CA); Erick Moyneur, L'ange-Gardien (CA); Alain Dury, Ste-Catherine-de-la-Jacques-Cartier (CA); Sylvain Gauthier, St-Augustin-de-Desmaures (CA)

(73) Assignee: ENDORECHERCHE. INC.

( * ) Notice: Subject to any disclaimer, the term of this patent is extended or adjusted under 35 U.S.C. 154(b) by 25 days.

(21) Appl. No.: 17/538,875

(22) Filed: Nov. 30, 2021

(65) Prior Publication Data

US 2022/0313703 A1    Oct. 6, 2022

Related U.S. Application Data

(60) Provisional application No. 63/119,813, filed on Dec. 1, 2020.

(51) Int. Cl.
| | | |
|---|---|---|
| *A61K 31/566* | (2006.01) | |
| *A61K 31/453* | (2006.01) | |
| *A61K 9/00* | (2006.01) | |
| *A61P 35/00* | (2006.01) | |
| *A61P 15/00* | (2006.01) | |

(52) U.S. Cl.
CPC .......... *A61K 31/566* (2013.01); *A61K 9/0034* (2013.01); *A61K 31/453* (2013.01); *A61P 15/00* (2018.01); *A61P 35/00* (2018.01)

(58) Field of Classification Search
CPC .. A61K 31/566; A61K 9/0034; A61K 31/453; A61P 15/00; A61P 35/00
See application file for complete search history.

(56) References Cited

FOREIGN PATENT DOCUMENTS

| WO | WO 94/16709 A2 | 8/1994 |
|---|---|---|
| WO | WO 2006/042409 A1 | 4/2006 |

OTHER PUBLICATIONS

Labrie, et al., Effect of intravaginal DHEA on serum DHEA and eleven of its metabolites in postmenopausal women, J. of Steroid Biochem. And Mol. Bio., vol. 111, Issues 3-5, pp. 178-194 (2008). (Year: 2008).*

Antoine, C., J. Vandromme, et al. (2008). "A survey among breast cancer survivors: treatment of the climacteric after breast cancer." Climacteric 11: 322-328.
Carter, J., C. Lacchetti, et al. (Feb. 2018). "Interventions to Address Sexual Problems in People With Cancer: American Society of Clinical Oncology Clinical Practice Guideline Adaptation of Cancer Care Ontario Guideline." J Clin Oncol 36(5): 492-511.
Colín-Val, Z., V.Y. González-Puertos, et al. (2017). "DHEA increases epithelial markers and decreases mesenchymal proteins in breast cancer cells and reduces xenograft growth." Toxicol Appl Pharmacol 333: 26-34.
Dimitrakakis, C., R.A. Jones, et al. (2004). "Breast cancer incidence in postmenopausal women using testosterone in addition to usual hormone therapy." Menopause 11(5): 531-535.
Fabian C.J., B.F. Kimler et al. (2015). "Clinical Trial of Acolbifene in Premenopausal Women at High Risk for Breast Cancer." Cancer Prev Res (Phila) 8(12): 1146-1155.
Gabrielson, M., K.M. Ubhayasekera, et al. (2020). "Inclusion of Endogenous Plasma Dehydroepiandrosterone Sulfate and Mammographic Density in Risk Prediction Models for Breast Cancer." Cancer Epidemiol Biomarkers Prev 29(3): 574-581.
Kotsopoulos, J., A.L. Shafrir et al. (2015). "The Relationship Between Bilateral Oophorectomy and Plasma Hormone Levels in Postmenopausal Women." Horm Cancer 6(1): 54-63.
Labrie, F. (1991). "Intracrinology" Mol Cell Endocrinol 78: C113-C118.
Labrie, F., V. Luu-The, et al. (2005). "Is DHEA a hormone? Starling Review." J Endocrinol 187: 169-196.
Labrie, F., A. Belanger et al. (2006). "Androgen glucuronides, instead of testosterone, as the new markers of androgenic activity in women." J Steroid Biochem Mol Biol 99: 182-188.
Labrie, F., L. Cusan, et al. (2008a). "Corrigendum to: Effect of intravaginal DHEA on serum DHEA and eleven of its metabolites in postmenopausal women." J Steroid Biochem Mol Biol 112: 169.
Labrie, F., L. Cusan, et al. (2008b). "Effect of Intravaginal DHEA on Serum DHEA and Eleven of its Metabolites in Postmenopausal Women." Journal Ster Biochem & Mol Biol 111: 178-194.
Labrie, F., D. Archer, et al. (2009). "Serum steroid levels during 12-week intravaginal dehydroepiandrosterone administration." Menopause 16: 897-906.
Labrie, F., C. Martel, et al. (2011). "Wide distribution of the serum dehydroepiandrosterone and sex steroid levels in postmenopausal women: role of the ovary?" Menopause 18(1): 30-43.
Luo, S., A. Sourla et al. (1997). "Combined Effects of Dehydroepiandrosterone and EM-800 on Bone Mass, Serum Lipids, and the Development of Dimethylbenz(A)Anthracene-Induced Mammary Carcinoma in the Rat." Endocrinology 138(10): 4435-4444.
Morales, L., P. Neven, et al. (2004). "Acute effects of tamoxifen and third-generation aromatase inhibitors on menopausal symptoms of breast cancer patients." Anti-Cancer Drugs 15: 753-760.
Stoll, B.A. (1999). "Dietary supplements of dehydroepiandrosterone in relation to breast cancer risk" Eur J Clin Nutr 53(10): 771-775.

* cited by examiner

*Primary Examiner* — Erich A Leeser
(74) *Attorney, Agent, or Firm* — Ostrolenk Faber LLP (57) ABSTRACT

The present invention relates to the intravaginal use of sex steroid precursor (e.g. DHEA) for the reduction of the incidence or recurrence of breast cancer in postmenopausal women. The dosage of sex steroid precursor is limited to 25 mg per day or less. Further administration of selective estrogen receptor modulator is disclosed for the above-reduction.

33 Claims, 5 Drawing Sheets

REDUCTION OF THE INCIDENCE OR RECURRENCE OF BREAST CANCER IN POSTMENOPAUSAL WOMEN TREATED WITH INTRAVAGINAL SEX STEROID PRECURSOR

CROSS REFERENCE TO RELATED APPLICATION

The present application claims the benefit of the priority under 35 U.S.C. § 119 of U.S. Provisional Application 63/119,813 filed Dec. 1, 2020, the contents of which are all incorporated herein by reference.

FIELD OF THE INVENTION

The present invention relates to the intravaginal use of sex steroid precursor (e.g. prasterone/dehydroepiandrosterone/ DHEA) for the reduction of the incidence or recurrence of breast cancer in postmenopausal women.

BACKGROUND

The prevalence of vaginal symptoms in postmenopausal breast cancer patients varies greatly, but vaginal itching/ irritation has been reported in up to 15%, vaginal dryness in up to 88%, and dyspareunia in up to 62% (Antoine et al. 2008; Morales et al. 2004). In the US, all prescription products indicated for vulvo-vaginal atrophy symptoms (VVA) are contraindicated for patients with a history of breast cancer with the exception of intravaginal prasterone (6.5 mg suppository). The off-label use of vaginal estrogens in patients with breast cancer remains controversial and safety studies are not available. The American Society of Clinical Oncology is supporting the use of intravaginal prasterone for women with current or a history of breast cancer who are on aromatase inhibitors and have not responded to previous treatment (Carter et al. 2018).

It is known from WO 94/16709 that the sex steroid precursor DHEA can be utilized for the treatment and/or prevention of vulvovaginal atrophy or breast cancer. WO 06/42409 teaches inter alia novel methods for treating or reducing the likelihood of acquiring vaginal dysfunction, particularly of vaginal dryness and dyspareunia, frequently accompanied by sexual dysfunction and low sexual desire by intravaginal administration of sex steroid precursors like DHEA but not for breast cancer. WO 09/21323 discloses certain DHEA doses and compositions, particularly vaginal suppositories, for treating menopause symptoms like vaginal atrophy, dyspareunia and dryness as well as claimed prevention and/or treatment of breast cancer (see also abstract).

Since, at the doses used, DHEA acts exclusively in the vagina following its local conversion into androgens and/or estrogens by the mechanisms of intracrinology (Labrie 1991; Labrie, Luu-The et al, 2005) without systemic exposure or significant changes in serum testosterone or estradiol (Labrie, Cusari et a l 2006a; Labrie, Cusan et al. 2008b), the presently-discovered effect of DHEA challenges the existing knowledge on the prevention of breast cancer in postmenopausal women.

All androgens in women derive from the transformation of DHEA into testosterone and dihydrotestosterone (DHT) in peripheral tissues in both pre- and postmenopause. Moreover, serum DHEA levels start decreasing by the age of 30 years with a 60% loss already observed at time of menopause with limited contribution of the ovary (Labrie 1991; Labrie, Luu-The et al, 2005; Labrie, Bélanger et al. 2006; Labrie, Martel et al. 2011).

SUMMARY OF THE INVENTION

The present invention relates to the intravaginal use of sex steroid precursor (e.g. prasterone/dehydroepiandrosterone/ DHEA) for the reduction of the incidence or recurrence of breast cancer in postmenopausal women.

In one embodiment, the invention provides a method for the reduction of the incidence or the recurrence of breast cancer in postmenopausal women with an intravaginal sex steroid precursor selected from the group consisting of dehydroepiandrosterone, 4-androstene-3,17-dione and androst-5-ene-3β,17β-diol, wherein said sex steroid precursor is administered at a therapeutic amount of 25 mg per day or less.

The said therapeutic amount does not increase the circulating levels of sex steroid precursor above the values found in normal postmenopausal women when the said sex steroid precursor is administered. The average 24 hour level of circulating dehydroepiandrosterone is below 4 ng/mL when dehydroepiandrosterone is administered. The average 24 hour level of circulating 4-androstene-3,17-dione is below 0.7 ng/mL when 4-androstene-3,17-dione is administered. The average 24 hour level of circulating androst-5-ene-3β, 17β-diol is below 0.6 ng/mL when androst-5-ene-3β,17β-diol is administered.

It is preferred that the sex steroid precursor is dehydroepiandrosterone.

It is preferred that the therapeutic amount of intravaginal sex steroid precursor is 6.5 mg per day or less.

In some embodiments, the methods of the invention discussed herein are used to prevent or treat vulvo-vaginal atrophy symptoms selected from the group consisting of vaginal dryness, burning and itching, and dyspareunia.

In other embodiments, the methods of the invention discussed herein are used to prevent or treat vasomotor symptoms selected from the group consisting of hot flushes and night sweats.

In another embodiment, the invention provides a method for the reduction of the incidence or the recurrence of breast cancer in postmenopausal women with an intravaginal sex steroid precursor selected from the group consisting of dehydroepiandrosterone, 4-androstene-3,17-dione and androst-5-ene-3β,17β-diol used in conjunction with a selective estrogen receptor modulator, as part of a combination therapy.

It is preferred that the selective estrogen receptor modulator is selected from the group consisting of Tamoxifen, Toremifene, CC 8490, SERM 3471, HMR 3339, HMR 3656, Raloxifene, LY 335124, LY 326315, Arzoxifene (LY 353381), Pipendoxifene (ERA 923), Bazedoxifene (TSE 424, WAY 140424), Oporia (Lasofoxifene), EM-652, EM-800, EM-652-HCl (acolbifene, EM-1538), 4-hydroxy-Tamoxifen, 4-hydroxy-Toremifene, Droloxifene, LY 335563, GW-5638, Idoxifene, Levormeloxifene, Iproxifen (TAT-59), Ospemifene (FC 1271), Fispemifene, Centchroman, CHF 4227, LY 2066948, LY 2120310, Sivifene, SR 16234, Clomiphene, Enclomiphene, Zuclomiphene, GW 7603, BL 3040, SRI 16158, SR 16157, SRI 16137, SR 16137, Rad 1901, (+)-3-(4-hydroxyphenyl)-2-[4-[2-(1-piperidinyl) ethoxy]phenyl]-4-(trifluoromethyl)-2H-1-benzopyran-7-ol, Femarelle, Nafoxidine and Endoxifen.

It is preferred that the selective estrogen receptor modulator is acolbifene.

In another embodiment, the invention provides a method for the reduction of the incidence or the recurrence of breast cancer in postmenopausal women with an oral sex steroid precursor selected from the group consisting of dehydroepiandrosterone, 4-androstene-3,17-dione and androst-5-ene-3β,17β-diol, wherein said sex steroid precursor is administered at a therapeutic amount of 100 mg per day or less.

It is preferred that the therapeutic amount of oral sex steroid precursor is 25 mg per day or less.

In another embodiment, the invention provides a method for the reduction of the incidence or the recurrence of breast cancer in postmenopausal women with a topical sex steroid precursor selected from the group consisting of dehydroepiandrosterone, 4-androstene-3,17-dione and androst-5-ene-3β,17β-diol, wherein said sex steroid precursor is administered at a therapeutic amount of 400 mg per day or less.

It is preferred that the therapeutic amount of topical sex steroid precursor is 100 mg per day or less.

In another embodiment, the invention provides a method for the reduction of the incidence or the recurrence of breast cancer in postmenopausal women with an oral or topical sex steroid precursor selected from the group consisting of dehydroepiandrosterone, 4-androstene-3,17-dione and androst-5-ene-3β,17β-diol used in conjunction with a selective estrogen receptor modulator, as part of a combination therapy.

DETAILED DESCRIPTION OF THE INVENTION

Figure 5:
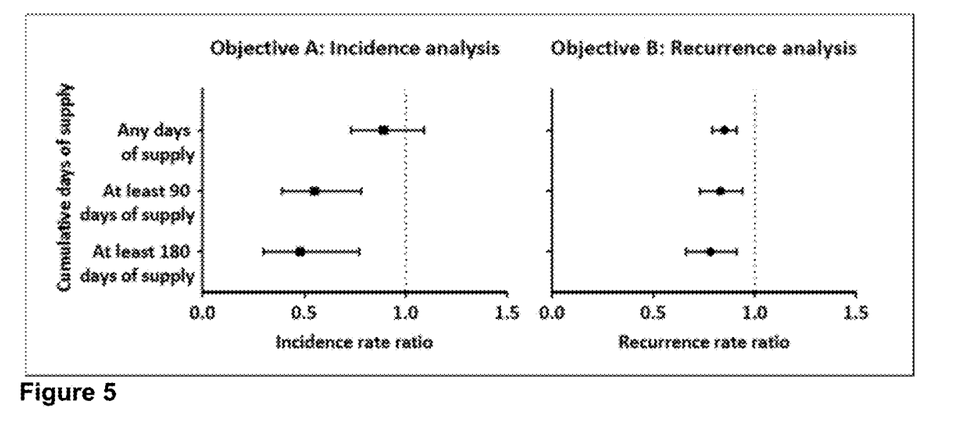
FIG. 5 shows incidence and recurrence of breast cancer among prasterone and untreated VVA women which are stratified by drug exposure.

The present retrospective data show that a significant reduction in both the incidence and recurrence of breast cancer were found in the prasterone groups compared to the untreated VVA groups once a minimum exposure threshold either 90 days or 180 days of supply was put in place (Table 2 and FIG. 5). It demonstrates that the use of intravaginal prasterone significantly reduces not only the incidence of breast cancer, but also its recurrence amongst patients with a history of breast cancer.

In detail, the longer patients remained on treatment with prasterone, the more the incidence ratio was reduced. With at least 90 days of supply, incidence ratio was 0.55 (95% CI: 0.39-0.78) with a statistically significant p value of 0.0008. In a dose response manner, a threshold of 180 days of supply even further reduced the incidence of breast cancer, down to an incidence ratio of 0.48 (95% CI: 0.30-0.77), with a statistically significant p value of 0.0021.

Moreover, the longer patients with a history of breast cancer remained on treatment with prasterone, the more the recurrence ratio was reduced. With at least 90 days of supply, recurrence ratio was 0.83 (95% CI: 0.73-0.94) with a statistically significant p value of 0.0045. Again, in a dose response manner, a threshold of 180 days of supply even further reduced the percentage of recurrence of breast cancer in the prasterone group, down to a recurrence ratio of 0.78 (95% CI: 0.66-0.91), with a statistically significant p value of 0.0021.

On the other hand, a review on dietary supplements of dehydroepiandrosterone in relation to breast cancer risk has concluded that late promotion of breast cancer in postmenopausal women may be stimulated by prolonged intake of DHEA, and the risk may be increased by the endocrine abnormality associated with pre-existing abdominal obesity. Caution is advised in the use of dietary supplements of DHEA particularly by obese postmenopausal women (Stoll 1999). However, no clinical study has confirmed that dietary supplements of dehydroepiandrosterone increases the risk of breast cancer in postmenopausal women.

According to the literature, high levels of circulating sex hormones and its precursors are associated with an increase of the risk of breast cancer in postmenopausal women. Recent risk prediction models for breast cancer have shown that dehydroepiandrosterone sulfate (DHEAS) and percentage mammographic density were independently and positively associated with breast cancer risk (P=0.007 and P<0.001, respectively) for postmenopausal women, but not premenopausal women. No significant association was seen for dehydroepiandrosterone (DHEA). Thus, DHEAS and mammographic density are independent risk factors for breast cancer and improve risk discrimination for postmenopausal breast cancer (Gabrielson et al. 2020).

Based on the pivotal results of the Example and the Gabrielson's reference, the applicant believes that the administration of intravaginal DHEA should permit some systemic absorption without important increase of the levels of circulating DHEAS. In other words, the present invention permits to increase the levels of the circulating sex steroid precursor DHEA by intravaginal administration in order to reach peripheral tissues (e.g. mammary glands) knowing that 60% of serum DHEA levels are lost at the menopause and androgens (in vivo converted from DHEA) are beneficial to protect mammary glands. Moreover, the applicant believes that a too large DHEA dosage could induce a loss of the beneficial effect observed in the described Example on the reduction of the incidence or recurrence of breast cancer. Consequently, a DHEA dosage range becomes necessary. The applicant postulates that the intravaginal DHEA is administered at a therapeutical amount of 25 mg per or less. This is equivalent to a therapeutic amount which does not increase the circulating levels of DHEA above the values found in normal postmenopausal women, or 4 ng/mL based on WO 09/21323 (Examples 1 and 3).

In detail, FIG. 7 of WO 09/21323 shows average 24-hour serum concentration ($AUC_{0-24h}/24$) of DHEA, 5-Diol, DHEA-S, 4-Dione, Testo and DHT measured on Day 1 or Day 7 following once daily administration of vaginal suppositories (ovules, pessaries or inserts) containing 0%, 0.5% (6.5 mg), 1.0% (13 mg) or 1.8% (23.4 mg) of DHEA in Witepsol H-15. Data are expressed as means ±SEM (n=8 to 10). Serum steroid concentrations measured in 30-35 year-old premenopausal women are added as reference. Data are expressed as mean (n=47) while the $5^{th}$ and $95^{th}$ centiles are indicated (dashed lines). *, p<0.05, **, p<0.01, experimental (Day 7) versus placebo (Day 7). Moreover, FIG. 30 of WO 09/21323 shows similar data with 0.5% DHEA only in addition to serum steroid concentrations measured in 30-35 year-old premenopausal women (n=47) as well as in 55-65 year-old postmenopausal (n=369) women are added as reference data which are expressed as means and $5^{th}$ and $95^{th}$ centiles (dashed lines). The upper limit of serum DHEA concentration in 55-65 year-old postmenopausal women in FIG. 30A corresponds to the average 24-hour serum concentration of DHEA on Day 7 of the said 1.8% DHEA suppositories, namely around 4 ng/m L. This value coincides with the average value of serum DHEA concentration in 30-35 year-old premenopausal women (see FIGS. 7A and 30A in WO 09/21323). Thus, the upper limit of DHEA dosage was established to 25 mg per day (after rounding off 23.4 mg). Moreover, the average 24-hour serum concentration of DHEAS on Day 7 of the said 1.8% DHEA suppositories is significantly higher than the placebo control and lower than the upper limit observed in 55-65 year-old postmenopausal women (see FIGS. 7C and 30C of WO 09/21323) which reinforces the postulate that 25 mg per day is the upper limit of intravaginal DHEA dosage. The risk of breast cancer due to the high levels of circulating DHEAS is attenuated with the proposed DHEA dosage range.

The same previous analysis could be done with the other exogenous intravaginal sex steroid precursors, namely 4-androstene-3,17-dione and androst-5-ene-3β,17β-diol where the upper dosage should be around 25 mg per day as DHEA. In detail, the therapeutic amount does not increase the circulating levels of 4-androstene-3,17-dione above the values found in normal postmenopausal women when 4-androstene-3,17-dione is administered. The upper limit is 0.7 ng/mL based on FIG. 31A of WO 09/21323 (55-65 year-old postmenopausal women). Furthermore, the therapeutic amount does not increase the circulating levels of androst-5-ene-3β,17β-diol above the values found in normal postmenopausal women when androst-5-ene-3β,17β-diol is administered. The upper limit is 0.6 ng/mL based on FIG. 30B of WO 09/21323 (55-65 year-old postmenopausal women). Consequently, 4-androstene-3,17-dione (4-dione) and androst-5-ene-3β,17β-diol (5-Diol) can be used instead of the preferred dehydroepiandrosterone (DHEA) but not dehydroepiandrosterone sulfate (DHEAS).

A manner to confirm the validity of our dosage range approach is to mention that most studies have reported that an oophorectomy performed after natural menopause does not protect against breast cancer risk (Kotsopoulos et al. 2016). Furthermore, the applicant has found that oophorectomy has decreased the levels of circulating sex steroids including precursors and metabolites by around 20% (Labrie et al. 2011). In Table 3, the circulating levels of all studied steroids are increased by 25% to 125% versus baseline levels with intravaginal 1.0% DHEA (13 mg), specially 25% increasement with DHEAS (close to the said 20%). This suggests that the intravaginal administration of DHEA at 13 mg per day is permitted but the 23.4 mg dose (1.8%) is probably borderline for the positive effect described in the Example.

The Applicant believes that oral and topical administration of DHEA should be used with precaution for the present invention because the average 24 hour serum concentration of DHEA at Day 14 is higher than 4 ng/mL (see FIG. 16A of WO 09/21323) using capsules at 100 mg/day and cream or gel at 400 mg/day. At these dosages, the increase of the levels of circulating DHEAS is also important specially with oral administration due to gastrointestinal metabolism (see FIG. 19A of WO 09/21323). In Table 3, the ratio of $AUC_{0-24h}$ values at $14^{th}$ day of dosing on predosing values ($14^{th}$/basal) are depicted for the studied steroids for DHEA capsules (100 mg/day) and DHEA cream (400 mg/day) obtained from Table 5 of WO 09/21323. Moreover, the ratio of the serum concentration at Week 12 of dosing on predosing values (12 w/basal) are also depicted for the studied steroids for DHEA suppositories (6.5 mg/day and 13 mg/day) which are calculated from Table 1 of the Labrie's reference (Labrie et al. 2009). The $14^{th}$/basal ratio for DHEAS is 9.73 and 2.04 for oral capsule and topical cream, respectively but the 12 w/basal is 1.04 and 1.25 for intravaginal suppositories at 6.5 mg and 13 mg, respectively. However, lower DHEA doses in oral formulation (<100 mg/day) and topical formulation (<400 mg/day) could be interesting when the therapeutic amounts of sex steroid precursor do not increase the circulating levels of the said sex steroid precursor above the values found in normal postmenopausal women (e.g. 4 ng/mL of DHEA) when the said sex steroid precursor is administered (optimization data are not available from our research group but could be obtained using the above strategy with lower oral and topical doses of sex steroid precursor). On the other hand, the efficacy on the prevention or the treatment of vulvo-vaginal atrophy symptoms could be lower when the sex steroid precursor is not administered locally (local intravaginal administration with low dosages is preferable). In summary, the low increases of serum steroids with intravaginal formulation is attractive knowing that a 6.5 mg DHEA suppository administered once daily reduces the incidence or recurrence of breast cancer in postmenopausal women as described in the Example.

As mentioned in the Background section, WO 94/16709 discloses the prevention or treatment of breast cancer with DHEA but there is no working example with intravaginal formulation or breast cancer data. Moreover, WO 94/16709 teaches a concentration of at least 7% by weight relative to the total pharmaceutical composition for percutaneous or transmucosal delivery of sex steroid precursor which is much higher than the upper 1.8% limit (vaginal suppository) described in the present invention. Furthermore, the targeted levels of serum DHEA in WO 94/16709 is between 4 and 10 μg/L (or ng/mL) which is higher than the upper 4 ng/mL limit of the present invention.

WO 09/21323 has claimed the prevention of breast cancer in postmenopausal women with sex steroid precursor without supporting data. Claim 1 of WO 09/21323 contains a proviso saying that "without increasing the circulating level of estradiol above the values found in normal postmenopausal women in order to avoid the risk of breast and uterine cancer". In fact, none of the working DHEA formulations in the description of WO 09/21323 are able to reach an average 24-hour serum estradiol concentration over 10 pg/mL. In other words, all DHEA dosages and administration modes are permissible to treat menopausal symptoms in WO 09/21323. In the present invention, the therapeutic amount of intravaginal sex steroid precursor is limited to a maximum of 25 mg/day due to our intention to avoid important increase of the levels of circulating DHEAS which is a factor of breast cancer risk in postmenopausal women.

The unexpected successful low intravaginal sex steroid precursor dosage (e.g. 6.5 mg of DHEA administered once daily in the Example) in the reduction of incidence and recurrence of breast cancer in postmenopausal women is explained by the increase of the levels of the circulating sex steroid precursor which is in vivo converted to androgens in the mammary glands. It is well known that androgens have a protecting role in mammary glands. It is supported by the reduction of the breast cancer incidence in postmenopausal women with testosterone supplements (Dimitrakakis et al 2004). At this low dosage, the in vivo conversion to androgens of sex steroid precursor is more important than to estrogens in mammary glands. In other words, the lost of serum DHEA at menopause is compensated. On the other hand, the mechanism of action of the observed effect could be different of the androgen receptor pathway (Colín-Val et al. 2017).

It is well known that selective estrogen receptor modulators (SERMs) are useful in the prevention of breast cancer. Consequently, a SERM can be combined with the intravaginal sex steroid precursor (oral and topical administration are also acceptable at low doses) to increase the efficacy on the reduction of the incidence or the recurrence of breast cancer in postmenopausal women.

The selective estrogen receptor modulator is selected from the group comprising of Tamoxifen, Toremifene, CC 8490, SERM 3471, HMR 3339, HMR 3656, Raloxifene, LY 335124, LY 326315, Arzoxifene (LY 353381), Pipendoxifene (ERA 923), Bazedoxifene (TSE 424, WAY 140424), Oporia (Lasofoxifene), EM-652, EM-800, EM-652-HCl (acolbifene, EM-1538), 4-hydroxy-Tamoxifen, 4-hydroxy-Toremifene, Droloxifene, LY 335563, GW-5638, Idoxifene, Levormeloxifene, Iproxifen (TAT-59), Ospemifene (FC 1271), Fispemifene, Centchroman, CHF 4227, LY 2066948, LY 2120310, Sivifene, SR 16234, Clomiphene, Enclomiphene, Zuclomiphene, GW 7603, BL 3040, SRI 16158, SR 16157, SRI 16137, SR 16137, Rad 1901, (+)-3-(4-hydroxyphenyl)-2-[4-[2-(1-piperidinyl)ethoxy]phenyl]-4-(trifluoromethyl)-2H-1-benzopyran-7-ol, Femarelle, Nafoxidine and Endoxifen.

The preferred SERM is acolbifene. A clinical trial using 20 mg once daily of oral acolbifene in premenopausal women at high risk for breast cancer show a decrease of the biomarker Ki-67 (Fabian et al. 2015). The SERM Tamoxifen at 5 mg/d for 3 years can halve the recurrence of breast intraepithelial neoplasia where 55% of women are menopaused in this study (DeCerisi et al. 2019). The applicant has shown that the additive inhibitory effects of DHEA and EM-800 (dipivaloate of the free-salt of acolbifene) on the development of DMBA-induced mammary carcinoma in the rat, thus suggesting the potential benefits of such a combination for the prevention of breast cancer in women while preserving or even increasing bone mass and maintaining a favorable lipid profile (Luo et al. 1997).

SERMs administered in accordance with the invention are preferably administered in a dosage range between 0.01 to 5 mg/kg of body weight per day (preferably 0.05 to 1.0 mg/kg), with 5 mg per day, especially 10 mg per day, in two equally divided doses being preferred for a person of average body weight when orally administered, or in a dosage range between 0.003 to 3.0 mg/kg of body weight per day (preferably 0.015 to 0.3 mg/mL), with 1.5 mg per day, especially 3.0 mg per day, in two equally divided doses being preferred for a person of average body weight when parentally administered (i.e. intramuscular, subcutaneous or percutaneous administration). Preferably the SERMs are administered together with a pharmaceutically acceptable diluent or carrier.

The applicants believe that the present invention can be applied to the premenopausal women in addition to the postmenopausal women as described in the below working example. On the other hand, the present invention (breast cancer) can be applied to the reduction of the incidence or the recurrence of other cancers sensible to hormones like uterine, endometrial and ovarian cancers.

EXAMPLE

The example below is intended only to illustrate a particular embodiment of the present invention and is not meant to limit the scope of the invention in any manner.

Objectives

Primary Objectives

We set out to assess the 1-year incidence rate of breast cancer among women treated with prasterone compared to matched controls of untreated VVA women (Objective A). We also assessed the 1-year recurrence rate of breast cancer among women treated with prasterone with a history of breast cancer compared to matched controls of untreated VVA women (Objective B).

Exploratory Objectives

In order to evaluate whether total exposure to prasterone in the follow-up window alters the results of the primary objectives A and B, we used sensitivity analyses to stratify patients based on cumulative days of supply.

Methods

Study Design and Key Entry Criteria

Figure 1:
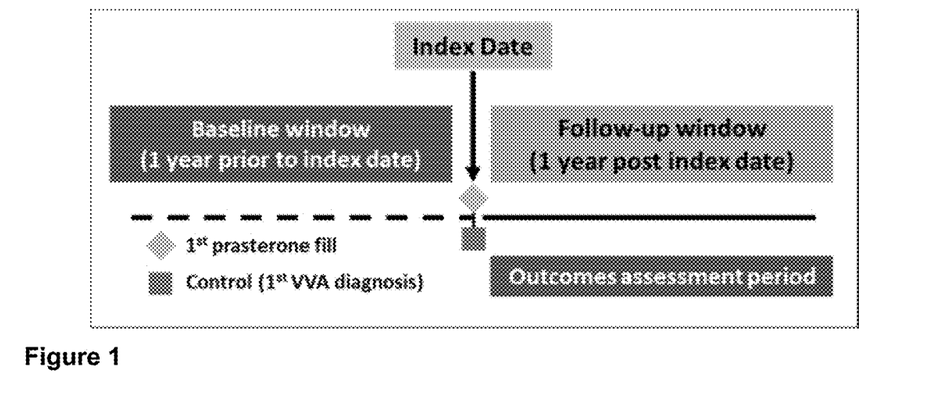
FIG. 1 shows index date definition.
Figure 2:
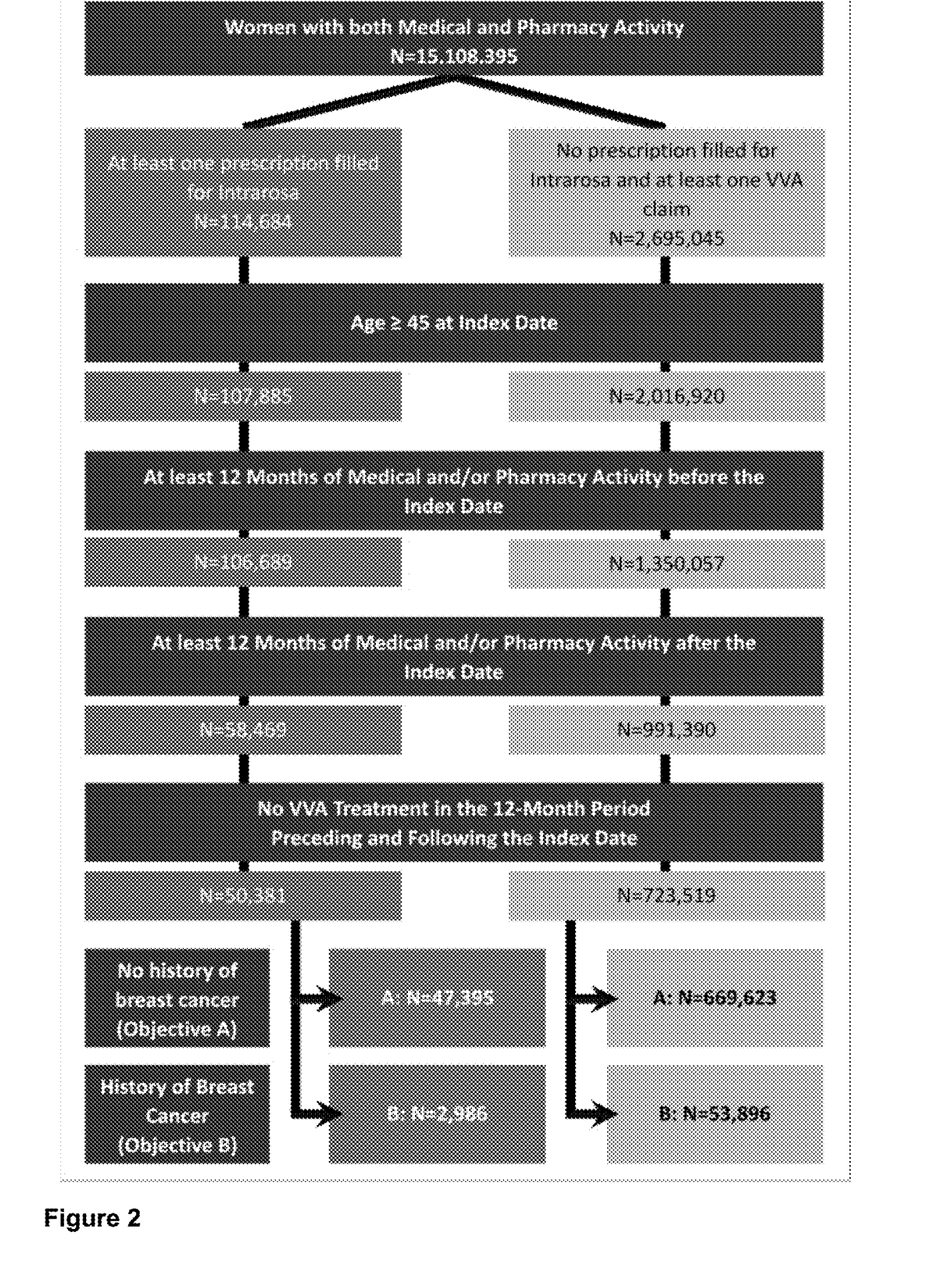
FIG. 2 shows attrition.

This retrospective cohort analysis was based on claims data from the Integrated Dataverse (IDV) database from Symphony Health Solutions. Data included in the analysis spanned a 5-year period from February 2015 through January 2020. For both objectives, the index date was defined as the first prasterone prescription fill date for treated women and as the initial VVA diagnosis date for untreated women (FIG. 1). Data were included from women who were at least 45 years of age and had at least one year of data available before and after the index date. Women treated with vaginal estrogen or ospem ifene were excluded. History of breast cancer prior to the index date was assessed. Before matching, 47,395 patients with at least one prescription of intravaginal prasterone (6.5 mg suppository) filled and no history of breast cancer were included and 2,986 with a history of breast cancer. Before matching again, 669,623 women were included in the pool of untreated VVA patients without a history of breast cancer, and 53,896 with a history of breast cancer (FIG. 2).

Matching Criteria and Index Date

Figure 3:
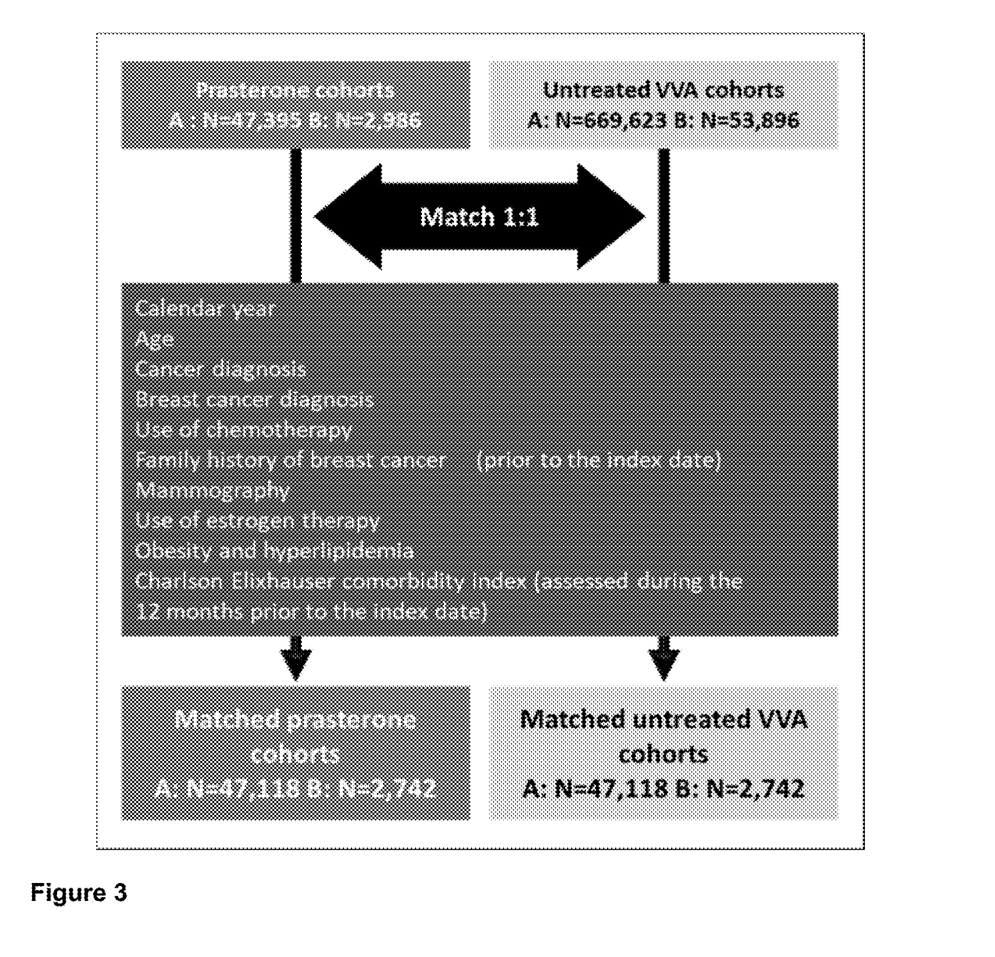
FIG. 3 shows matching criteria.

To ensure a balanced risk profile across treatment groups the women treated with prasterone were matched with a 1:1 ratio to untreated women based on the following parameters (FIG. 3):
Calendar year
Age
Prior to the index date:
  Cancer diagnosis
  Breast cancer diagnosis
  Use of chemotherapy
  Family history of breast cancer
  Mammography
  Use of estrogen therapy
  Obesity and hyperlipidemia
Assessed during the 12 months prior to the index date
  Charlson Elixhauser comorbidity index Results Primary objectives Objective A 47,118 patients with at least one prescription of intravaginal prasterone filled were included in objective A. Percentage of incidence was 0.39% in the prasterone group, and 0.44% in the untreated VVA group, resulting in an incidence ratio of 0.89 (95% Confidence Interval: 0.73-1.09). Even though there was a trend, there was no statistically significant difference (p=0.2643) in the incidence of breast cancer between the prasterone and the untreated VVA groups in all age groups (Table 1 and FIG. 4).

Objective B 2,742 patients with a history of breast cancer with at least one prescription of intravaginal prasterone filled were included in objective B. Percentage of recurrence of breast cancer was significantly lower in the prasterone group (34.21%) than in the untreated VVA group (40.37%). Resulting incidence ratio was 0.85 (95% CI: 0.79-0.91), with a p value below 0.0001 (Table 1 and FIG. 4).

Figure 4:
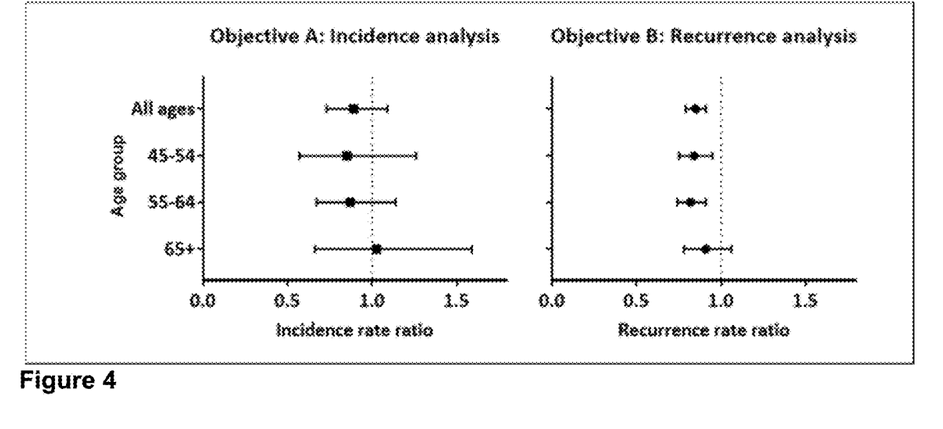
FIG. 4 shows incidence and recurrence of breast cancer among prasterone and untreated VVA women which are stratified by age.

For both objectives A and B, stratification of the data by age didn't impact the results (Table 1 and FIG. 4). For objective A, there was no statistical difference in the incidence of breast cancer between the prasterone group and the untreated VVA for patients between 45 to 54 years old, for patients between 55 and 64 years old, and for patients older than 65 years old. For objective B, there was a significant reduction of recurrence in all three age groups (Table 1 and FIG. 4).

Exploratory Objectives

Primary objectives A and B included all women meeting the inclusion criteria and having at least one prescription of prasterone filled. We then set minimum exposure thresholds to stratify patients based on the length of exposure. Thresholds were set at least 90 or 180 days of supply. Incidence (objective A) and recurrence (objective B) analyses were conducted in these new groups.

The longer patients remained on treatment with prasterone, the more the incidence ratio was reduced. With at least 90 days of supply, incidence ratio was 0.55 (95% CI: 0.39-0.78) with a statistically significant p value of 0.0008. In a dose response manner, a threshold of 180 days of supply even further reduced the incidence of breast cancer, down to an incidence ratio of 0.48 (95% CI: 0.30-0.77), with a statistically significant p value of 0.0021.

The longer patients with a history of breast cancer remained on treatment with prasterone, the more the recurrence ratio was reduced. With at least 90 days of supply, recurrence ratio was 0.83 (95% CI: 0.73-0.94) with a statistically significant p value of 0.0045. Again, in a dose response manner, a threshold of 180 days of supply even further reduced the percentage of recurrence of breast cancer in the prasterone group, down to a recurrence ratio of 0.78 (95% CI: 0.66-0.91), with a statistically significant p value of 0.0021.

Conclusions

A significant reduction in both the incidence and recurrence of breast cancer were found in the prasterone groups compared to the untreated VVA groups once a minimum exposure threshold either 90 days or 180 days of supply was put in place (Table 2 and FIG. 5). While the results are based on retrospective data, they nonetheless demonstrate that the use of intravaginal prasterone significantly reduces not only the incidence of breast cancer, but also its recurrence amongst patients with a history of breast cancer.

REFERENCES

Antoine, C., J. Vandromme, et al. (2008). "A survey among breast cancer survivors: treatment of the climacteric after breast cancer." *Climacteric* 11: 322-328.

Carter, J., C. Lacchetti, et al. (2018). "Interventions to Address Sexual Problems in People With Cancer: American Society of Clinical Oncology Clinical Practice Guideline Adaptation of Cancer Care Ontario Guideline." *J Clin Oncol* 36(5): 492-511.

Colin-Val, Z., V. Y. Gonzalez-Puertos, et al. (2017). "DHEA increases epithelial markers and decreases mesenchymal proteins in breast cancer cells and reduces xenograft growth." *Toxicol Appl Pharmacol* 333: 26-34.

Decensi, A., M. Puntoni, et al. (2019). "Randomized Placebo Controlled Trial of Low-Dose Tamoxifen to Prevent Local and Contralateral Recurrence in Breast Intraepithelial Neoplasia." *J Clin Oncol* 37(19): 1629-1637.

Dimitrakakis, C., R. A. Jones, et al. (2004). "Breast cancer incidence in postmenopausal women using testosterone in addition to usual hormone therapy." *Menopause* 11(5): 531-535.

Fabian C. J., B. F. Kimler et al. (2015). "Clinical Trial of Acolbifene in Premenopausal Women at High Risk for Breast Cancer." *Cancer Prev Res (Phila)* 8(12): 1146-1155.

Gabrielson, M., K. M. Ubhayasekera, et al. (2020). "Inclusion of Endogenous Plasma Dehydroepiandrosterone Sulfate and Mammographic Density in Risk Prediction Models for Breast Cancer." *Cancer Epidemiol Biomarkers Prev* 29(3): 574-581.

Kotsopoulos, J., A. L. Shafrir, et al. (2015). "The Relationship Between Bilateral Oophorectomy and Plasma Hormone Levels in Postmenopausal Women." *Horm Cancer* 6(1): 54-63.

Labrie, F. (1991). "Intracrinology" *Mol Cell Endocrinol* 78: C113-C118.

Labrie, F., V. Luu-The, et al. (2005). "Is DHEA a hormone? Starling Review." *J Endocrinol* 187: 169-196.

Labrie, F., A. Bélanger, et al. (2006). "Androgen glucuronides, instead of testosterone, as the new markers of androgenic activity in women." *J Steroid Biochem Mol Biol* 99: 182-188.

Labrie, F., L. Cusan, et al. (2008a). "Corrigendum to: Effect of intravaginal DHEA on serum DHEA and eleven of its metabolites in postmenopausal women." *J Steroid Biochem Mol Biol* 112: 169.

Labrie, F., L. Cusan, et al. (2008b). "Effect of Intravaginal DHEA on Serum DHEA and Eleven of its Metabolites in Postmenopausal Women." *Journal Ster Biochem & Mol Biol* 111: 178-194.

Labrie, F., D. Archer, et al. (2009). "Serum steroid levels during 12-week intravaginal dehydroepiandrosterone administration." *Menopause* 16: 897-906.

Labrie, F., C. Martel, et al. (2011). "Wide distribution of the serum dehydroepiandrosterone and sex steroid levels in postmenopausal women: role of the ovary?" *Menopause* 18(1): 30-43.

Luo, S., A. Sourla et al. (1997). "Combined Effects of Dehydroepiandrosterone and EM-800 on Bone Mass, Serum Lipids, and the Development of Dimethylbenz(A)Anthracene-Induced Mammary Carcinoma in the Rat." *Endocrinology* 138(10): 4435-4444.

Morales, L., P. Neven, et al. (2004). "Acute effects of tamoxifen and third-generation aromatase inhibitors on menopausal symptoms of breast cancer patients." *Anti-Cancer Drugs* 15: 753-760.

Stoll, B. A. (1999). "Dietary supplements of dehydroepiandrosterone in relation to breast cancer risk" *Eur J Clin Nutr* 53(10): 771-775.

TABLE 1

Incidence and recurrence of breast cancer among prasterone and untreated VVA women - Stratified by age

| | Objective A: Incidence analysis | | Objective B: Recurrence analysis | |
|---|---|---|---|---|
| | N | % of incidence (BrCa events) | N | % of recurrence (BrCa events) |
| All ages (≥45 years old) | | | | |
| Intravaginal prasterone | 47,118 | 0.39 (184) | 2,742 | 34.21 (938) |
| Untreated VVA | 47,118 | 0.44 (206) | 2,742 | 40.37 (1107) |
| Ratio (95% CI) | — | 0.89 (0.73-1.09) | — | 0.85 (0.79-0.91) |
| P-Value | — | 0.2643 | — | <0.0001 |
| 45 to 54 years old | | | | |
| Intravaginal prasterone | 13,032 | 0.34 (44) | 663 | 41.63 (276) |
| Untreated VVA | 13,032 | 0.40 (52) | 663 | 49.32 (327) |
| Ratio (95% CI) | — | 0.85 (0.57-1.26) | — | 0.84 (0.75-0.95) |
| P-Value | — | 0.4134 | — | 0.0049 |
| 55 to 64 years old | | | | |
| Intravaginal prasterone | 27,199 | 0.37 (100) | 1,426 | 31.42 (448) |
| Untreated VVA | 27,199 | 0.42 (115) | 1,426 | 38.22 (545) |
| Ratio (95% CI) | — | 0.87 (0.67-1.14) | — | 0.82 (0.74-0.91) |
| P-Value | — | 0.3054 | — | 0.0001 |
| 65 years old and older | | | | |
| Intravaginal prasterone | 6,887 | 0.58 (40) | 653 | 32.77 (214) |
| Untreated VVA | 6,887 | 0.57 (39) | 653 | 35.99 (235) |
| Ratio (95% CI) | — | 1.03 (0.66-1.59) | — | 0.91 (0.78-1.06) |
| P-Value | — | 0.1775 | — | 0.073 |

TABLE 2

Incidence and recurrence of breast cancer among prasterone and untreated VVA women - Stratified by drug exposure

| | Objective A: Incidence analysis | | | Objective B: Recurrence analysis | | |
|---|---|---|---|---|---|---|
| | N | % of incidence (BrCa events) | Median days of Supply (average) | N | % of incidence (BrCa events) | Median days of Supply (average) |
| Any days of supply | | | | | | |
| Intravaginal prasterone | 47,118 | 0.39 (184) | 56 (123) | 2,742 | 34.21 (938) | 56 (117) |
| Untreated VVA | 47,118 | 0.44 (206) | — | 2,742 | 40.37 (1107) | — |
| Ratio (95% CI) | — | 0.89 (0.73-1.09) | — | — | 0.85 (0.79-0.91) | — |
| P-Value | — | 0.2643 | — | — | <0.0001 | — |
| At least 90 days of supply | | | | | | |
| Intravaginal prasterone | 17,390 | 0.28 (48) | 224 (258) | 935 | 30.48 (285) | 224 (260) |
| Untreated VVA | 17,390 | 0.5 (87) | — | 935 | 36.68 (343) | — |
| Ratio (95% CI) | — | 0.55 (0.39-0.78) | — | — | 0.83 (0.73-0.94) | — |
| P-Value | — | 0.0008 | — | — | 0.0045 | — |
| At least 180 days of supply | | | | | | |
| Intravaginal prasterone | 10,140 | 0.25 (25) | 308 (344) | 558 | 30.29 (169) | 308 (344) |
| Untreated VVA | 10,140 | 0.51 (52) | — | 558 | 39.07 (218) | — |
| Ratio (95% CI) | — | 0.48 (0.30-0.77) | — | — | 0.78 (0.66-0.91) | — |
| P-Value | — | 0.0021 | — | — | 0.0021 | — |

TABLE 3

Comparison of the ratio of the serum steroid values on predosing values with several modes of DHEA administration

| steroids | oral DHEA capsule 100 mg/day $14^{th}$/basal$^a$ | topic DHEA cream 400 mg/day $14^{th}$/basal$^a$ | intravaginal DHEA suppository 6.5 mg/day 12 w/basal$^b$ | intravaginal DHEA suppository 13 mg/day 12 w/basal$^b$ |
|---|---|---|---|---|
| DHEA | 2.67 | 5.06 | 1.25 | 1.71 |
| 5-Diol | 2.38 | 4.63 | 1.46 | 2.25 |
| 4-Dione | 3.38 | 1.77 | 1.08 | 1.37 |
| T | 1.11 | 1.01 | 1.23 | 1.50 |
| $E_1$ | 1.27 | 1.18 | 1.22 | 1.32 |
| $E_2$ | 1.22 | 1.30 | 1.36 | 1.50 |
| DHEAS | 9.73 | 2.04 | 1.04$^c$ | 1.25$^c$ |
| $E_1S$ | 1.60 | 1.72 | 1.26 | 1.28 |
| ADT-G | 19.2 | 3.34 | 1.18 | 1.59 |
| 3α-Diol-G | 9.74 | 2.25 | 1.14(3G); 1.21(17G) | 1.56(3G); 1.78(17G) |

$^a$obtained from Table 5 of WO 09/21323
$^b$calculated from Table 1 of Labrie et al. 2009
$^c$the ratio $7^{th}$/basal is 1.03, 1.21 and 1.79 for 6.5, 13 and 23.4 mg/day (or 0.5%, 1.0% and 1.8%), respectively calculated from FIG. 7C of Labrie, Cusan et al. 2008a

What is claimed is:

1. A method of reducing the incidence or the recurrence of breast cancer in postmenopausal women comprising administering, to a human female in need of such reduction, a sex steroid precursor selected from the group consisting of dehydroepiandrosterone, 4-androstene-3,17-dione and androst-5-ene-3β,17β-diol, wherein said sex steroid precursor is administered intravaginally at a therapeutic amount of 25 mg per day or less.

2. The method of claim 1 wherein the said therapeutic amount does not increase the circulating levels of sex steroid precursor above the values found in normal postmenopausal women when the said sex steroid precursor is administered.

3. The method of claim 2 wherein the average 24 hour level of circulating dehydroepiandrosterone is below 4 ng/mL when dehydroepiandrosterone is administered.

4. The method of claim 2 wherein the average 24 hour level of circulating 4-androstene-3,17-dione is below 0.7 ng/mL when 4-androstene-3,17-dione is administered.

5. The method of claim 2 wherein the average 24 hour level of circulating androst-5-ene-3β,17β-diol is below 0.6 ng/mL when androst-5-ene-3β,17β-diol is administered.

6. The method of claim 1 wherein the sex steroid precursor is dehydroepiandrosterone.

7. The method of claim 1 wherein the therapeutic amount is 6.5 mg per day or less.

8. The method of claim 1 wherein the said reduction prevents or treats vulvo-vaginal atrophy symptoms selected from the group consisting of vaginal dryness, burning and itching, and dyspareunia.

9. The method of claim 1 wherein the said reduction prevents or treats vasomotor symptoms selected from the group consisting of hot flushes and night sweats.

10. The method of claim 1 further comprising a step of administering to said human female a therapeutic amount of a selective estrogen receptor modulator selected from the group consisting of Tamoxifen, Toremifene, CC 8490, SERM 3471, HMR 3339, HMR 3656, Raloxifene, LY 335124, LY 326315, Arzoxifene (LY 353381), Pipendoxifene (ERA 923), Bazedoxifene (TSE 424, WAY 140424), Oporia (Lasofoxifene), EM-652, EM-800, EM-652-HCl (acolbifene, EM-1538), 4-hydroxy-Tamoxifen, 4-hydroxy-Toremifene, Droloxifene, LY 335563, GW-5638, Idoxifene, Levormeloxifene, Iproxifen (TAT-59), Ospemifene (FC 1271), Fispemifene, Centchroman, CHF 4227, LY 2066948, LY 2120310, Sivifene, SR 16234, Clomiphene, Enclomiphene, Zuclomiphene, GW 7603, BL 3040, SRI 16158, SR 16157, SRI 16137, SR 16137, Rad 1901, (+)-3-(4-hydroxyphenyl)-2-[4-[2-(1-piperidinyl)ethoxy]phenyl]-4-(trifluoromethyl)-2H-1-benzopyran-7-ol, Femarelle, Nafoxidine and Endoxifen, as part of a combination therapy.

11. The method of claim 10 wherein the selective estrogen receptor modulator is acolbifene.

12. A method of reducing the incidence or the recurrence of breast cancer in postmenopausal women comprising administering, to a human female in need of such reduction, a sex steroid precursor selected from the group consisting of dehydroepiandrosterone, 4-androstene-3,17-dione and androst-5-ene-3β,17β-diol, wherein said sex steroid precursor is administered orally at a therapeutic amount of 100 mg per day or less.

13. The method of claim 12 wherein the said therapeutic amount does not increase the circulating levels of sex steroid precursor above the values found in normal postmenopausal women when the said sex steroid precursor is administered.

14. The method of claim 13 wherein the average 24 hour level of circulating dehydroepiandrosterone is below 4 ng/mL when dehydroepiandrosterone is administered.

15. The method of claim 13 wherein the average 24 hour level of circulating 4-androstene-3,17-dione is below 0.7 ng/mL when 4-androstene-3,17-dione is administered.

16. The method of claim 13 wherein the average 24 hour level of circulating androst-5-ene-3β,17β-diol is below 0.6 ng/mL when androst-5-ene-3β,17β-diol is administered.

17. The method of claim 12 wherein the sex steroid precursor is dehydroepiandrosterone.

18. The method of claim 12 wherein the therapeutic amount is 25 mg per day or less.

19. The method of claim 12 wherein the said reduction prevents or treats vulvo-vaginal atrophy symptoms selected from the group consisting of vaginal dryness, burning and itching, and dyspareunia.

20. The method of claim 12 wherein the said reduction prevents or treats vasomotor symptoms selected from the group consisting of hot flushes and night sweats.

21. The method of claim 12 further comprising a step of administering to said human female a therapeutic amount of a selective estrogen receptor modulator selected from the group consisting of Tamoxifen, Toremifene, CC 8490, SERM 3471, HMR 3339, HMR 3656, Raloxifene, LY 335124, LY 326315, Arzoxifene (LY 353381), Pipendoxifene (ERA 923), Bazedoxifene (TSE 424, WAY 140424), Oporia (Lasofoxifene), EM-652, EM-800, EM-652-HCl (acolbifene, EM-1538), 4-hydroxy-Tamoxifen, 4-hydroxy-Toremifene, Droloxifene, LY 335563, GW-5638, Idoxifene, Levormeloxifene, Iproxifen (TAT-59), Ospemifene (FC 1271), Fispemifene, Centchroman, CHF 4227, LY 2066948, LY 2120310, Sivifene, SR 16234, Clomiphene, Enclomiphene, Zuclomiphene, GW 7603, BL 3040, SRI 16158, SR 16157, SRI 16137, SR 16137, Rad 1901, (+)-3-(4-hydroxyphenyl)-2-[4-[2-(1-piperidinyl)ethoxy]phenyl]-4-(trifluoromethyl)-2H-1-benzopyran-7-ol, Femarelle, Nafoxidine and Endoxifen, as part of a combination therapy.

22. The method of claim 21 wherein the selective estrogen receptor modulator is acolbifene.

23. A method of reducing the incidence or the recurrence of breast cancer in postmenopausal women comprising administering, to a human female in need of such reduction, a sex steroid precursor selected from the group consisting of dehydroepiandrosterone, 4-androstene-3,17-dione and androst-5-ene-3β,17β-diol, wherein said sex steroid precursor is administered topically at a therapeutic amount of 400 mg per day or less.

24. The method of claim 23 wherein the said therapeutic amount does not increase the circulating levels of sex steroid precursor above the values found in normal postmenopausal women when the said sex steroid precursor is administered.

25. The method of claim 24 wherein the average 24 hour level of circulating dehydroepiandrosterone is below 4 ng/mL when dehydroepiandrosterone is administered.

26. The method of claim 24 wherein the average 24 hour level of circulating 4-androstene-3,17-dione is below 0.7 ng/mL when 4-androstene-3,17-dione is administered.

27. The method of claim 24 wherein the average 24 hour level of circulating androst-5-ene-3β,17β-diol is below 0.6 ng/mL when androst-5-ene-3β,17β-diol is administered.

28. The method of claim 23 wherein the sex steroid precursor is dehydroepiandrosterone.

29. The method of claim 23 wherein the therapeutic amount is 100 mg per day or less.

30. The method of claim 23 wherein the said reduction prevents or treats vulvo-vaginal atrophy symptoms selected from the group consisting of vaginal dryness, burning and itching, and dyspareunia.

31. The method of claim 23 wherein the said reduction prevents or treats vasomotor symptoms selected from the group consisting of hot flushes and night sweats.

32. The method of claim 23 further comprising a step of administering to said human female a therapeutic amount of a selective estrogen receptor modulator selected from the group consisting of Tamoxifen, Toremifene, CC 8490, SERM 3471, HMR 3339, HMR 3656, Raloxifene, LY 335124, LY 326315, Arzoxifene (LY 353381), Pipendoxifene (ERA 923), Bazedoxifene (TSE 424, WAY 140424), Oporia (Lasofoxifene), EM-652, EM-800, EM-652-HCl (acolbifene, EM-1538), 4-hydroxy-Tamoxifen, 4-hydroxy-Toremifene, Droloxifene, LY 335563, GW-5638, Idoxifene, Levormeloxifene, Iproxifen (TAT-59), Ospemifene (FC 1271), Fispemifene, Centchroman, CHF 4227, LY 2066948, LY 2120310, Sivifene, SR 16234, Clomiphene, Enclomiphene, Zuclomiphene, GW 7603, BL 3040, SRI 16158, SR 16157, SRI 16137, SR 16137, Rad 1901, (+)-3-(4-hydroxyphenyl)-2-[4-[2-(1-piperidinyl)ethoxy]phenyl]-4-(trifluoromethyl)-2H-1-benzopyran-7-ol, Femarelle, Nafoxidine and Endoxifen, as part of a combination therapy.

33. The method of claim 32 wherein the selective estrogen receptor modulator is acolbifene.

* * * * *